United States Patent
Doehner, Jr.

[11] Patent Number: 5,892,050
[45] Date of Patent: Apr. 6, 1999

[54] PROCESS FOR THE PREPARATION OF PYRIDINE DICARBOXYLATE DERIVATIVES

[75] Inventor: Robert Francis Doehner, Jr., Windsor, N.J.

[73] Assignee: American Cyanamid Company, Madison, N.J.

[21] Appl. No.: 14,546

[22] Filed: Jan. 28, 1998

[51] Int. Cl.⁶ .................................................. C07D 213/30
[52] U.S. Cl. ............................................ 546/318; 546/319
[58] Field of Search .................................. 546/318, 319

[56] References Cited

U.S. PATENT DOCUMENTS

| | | | |
|---|---|---|---|
| 4,656,283 | 4/1987 | Doehner | 546/170 |
| 4,758,667 | 7/1988 | Szczepanski et al. | 546/167 |
| 4,997,947 | 3/1991 | Szczepanski et al. | 544/180 |
| 5,252,538 | 10/1993 | Cross et al. | 504/156 |

OTHER PUBLICATIONS

R.A. Abramovitch, *Pyridine and its Derivatives Supplement Part Three,* John Wiley & Sons, pp. 268–330 (1974).

*Primary Examiner*—Jane Fan
*Attorney, Agent, or Firm*—John W. Hogan, Jr.

[57] ABSTRACT

There is provided a single vessel process for the preparation of a pyridine dicarboxylate compound of formula I

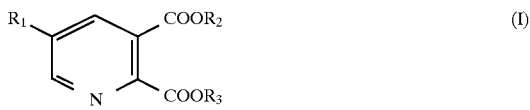

via the sequential condensation of an alkyl vinyl ether with Vilsmeier reagent, oxalacetate and an ammonia source.

15 Claims, No Drawings

PROCESS FOR THE PREPARATION OF PYRIDINE DICARBOXYLATE DERIVATIVES

BACKGROUND OF THE INVENTION

Pyridine-2,3-dicarboxylc acids and esters are building blocks for numerous bio-active products, particularly imidazolinone herbicides, for example U.S. Pat. No. 4,758,667. Known methods to prepare pyridine-2,3-dicarboxylate derivatives via the oxidation of a suitable quinoline or alkylpyridine precursor are often plagued by the use of costly oxidants such as $KMnO_4$, $H_2Cr_2O_7$, $SeO_2$ and the like; by long reaction time cycles such as in the use of ozone, electrolysis and the like; and by undesirable side reactions such as decarboxylation, N-oxide formation and the like. Therefore, new methods to construct the desired pyridine dicarboxylate product are continually being sought.

It has now been found that a rapid one vessel process to prepare a pyridine-2,3-dicarboxylate derivative is readily obtained via the sequential condensation of the appropriate alkyl vinyl ether with Vilsmeier reagent, oxalacetate and an ammonia source.

SUMMARY OF THE INVENTION

The present invention provides an efficient and effective process for the preparation of pyridine-2,3-dicarboxylate derivatives of formula I

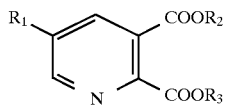  (I)

wherein $R_1$ is H or $C_1$–$C_4$alkyl optionally substituted with $C_1$–$C_4$alkoxy or halogen; and $R_2$ and $R_3$ are each independently $C_1$–$C_6$alkyl which comprises reacting an alkyl vinyl ether compound of formula II

  (II)

wherein the formula II compound is the cis isomer, the trans isomer or a mixture thereof, R is $C_1$–$C_4$alkyl and $R_1$ is as defined for formula I with at least one molar equivalent of Vilsmeier reagent optionally in the presence of a first solvent to form a first intermediate;

2) reacting said first intermediate with at least one molar equivalent of an oxalacetate of formula III $$\underset{O}{\overset{COOR_2}{\diagup}}\diagdown COOR_3 \qquad (III)$$

wherein $R_2$ and $R_3$ are as defined for formula I in the presence of at least two molar equivalents of a base to form a second intermediate; and 3) reacting said second intermediate with an ammonia source optionally in the presence of a second solvent to form the formula I pyridine diester product.

Compounds of formula I are useful in the preparation of imidazolinone herbicidal agents.

DETAILED DESCRIPTION OF THE INVENTION

Among the methods known to prepare pyridine 2,3-dicarboxylate derivatives are degradative methods such as oxidation of the appropriately substituted quinoline or alkylpyridine precursors. However, oxidation procedures often are costly and hazardous. Advantageously, it has now been found that pyridine-2,3-dicarboxylate derivatives of formula I may be effectively prepared in a single vessel via the sequential condensation of a suitable alkyl vinyl ether of formula II with Vilsmeier reagent, an oxalacetate of formula III and an ammonia source. The reaction is shown in Flow Diagram I, wherein $X^\ominus$ represents $Cl^\ominus$ or $PO_2Cl_2^\ominus$.

Flow Diagram I

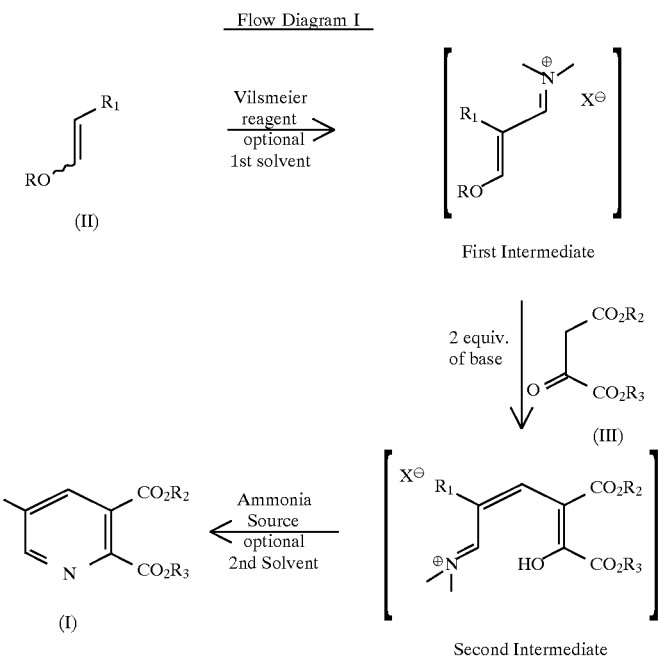

In accordance with the process of the invention, an alkyl vinyl ether of formula II, which may be the cis isomer or the trans isomer or a mixture thereof, may be reacted with at least one molar equivalent of Vilsmeier reagent optionally in the presence of a first solvent to form a first intermediate (a vinylogous imidate salt), which may then be reacted with at least one molar equivalent of an oxalacetate of formula III in the presence of at least two molar equivalents of a base, preferably an organic amine base, to form a second intermediate (an iminium salt), which may be reacted with an ammonia source optionally (and preferably) in the presence of a second solvent to form the desired formula I pyridine-2,3-dicarboxylate product.

The term Vilsmeier reagent, as used in the specification and claims, designates the in situ product of the reaction of dimethyl formamide with an activating agent such as oxalyl chloride, phosgene, phosphorous oxychloride, thionyl chloride, and the like and may be illustrated as an immonium salt of formula IV or the analogues thereof wherein $X^\ominus$ represents $Cl^\ominus$ or $PO_2Cl_2^\ominus$.

$$(CH_3)_2N^\oplus = CHCl\ X^\ominus \qquad (IV)$$

The term halogen as used in the specification and claims designates Cl, Br, I or F.

Solvents suitable for use as the first solvent in the inventive process may be any inert organic solvent such as a hydrocarbon, e.g. hexanes, pentanes, heptanes and the like; a halogenated hydrocarbon, e.g. methylene chloride, chloroform, dichloroethane, and the like, preferably dichloroethane or methylene chloride; an aromatic hydrocarbon, e.g. benzene, toluene, xylene and the like; a halogenated aromatic hydrocarbon, e.g. chlorobenzene, o-dichlorobenzene, or mixtures thereof. Preferably the reaction is conducted with a first solvent and preferably the first solvent is a halogenated hydrocarbon such as dichloroethane or methylene chloride.

Bases suitable for use in the inventive process are organic amines such as triethylamine, pyridine, lutidine, N,N-dimethylpiperidine, N-methylpyrrolidine and the like, preferably triethylamine or pyridine.

Ammonia sources suitable for use in the process of the invention may be any of the conventional means for producing $NH_3$ in situ, including ammonia gas, ammonium salts, and the like, preferably ammonium salts such as ammonium acetate, ammonium sulfamate, and the like.

Solvents suitable for use as the second solvent in the inventive process are protic solvents such as water; alcohols such as $C_1$–$C_4$ alkanols e.g. ethanol, methanol, propanol, butanol and the like, preferably ethanol; organic acids such as $C_1$–$C_4$ carboxylic acids e.g. acetic acid, propionic acid and the like, preferably acetic acid.

The rate of formation of the reaction product is generally directly related to the reaction temperature. In general, lower temperatures will decrease the rate of reaction and higher temperatures will increase the rate of reaction. However, excessively high temperatures are not desired and may lead to a decrease in product yield and purity. Preferable temperatures range from about 0° C. to 120° C.

In order to facilitate a further understanding of the invention, the following examples are set forth primarily for the purpose of illustrating certain more specific details thereof. The invention is not to be limited thereby except as defined in the claims. The term NMR designates nuclear magnetic resonance.

EXAMPLE 1

Preparation of Diethyl Pyridine-2,3-dicarboxylate

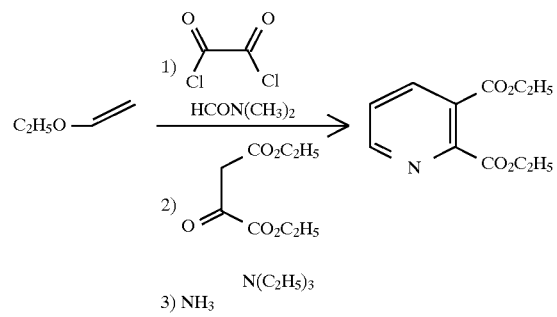

A soution of dimethyl formamide (73 g, 1.00 mole) in ethylene dichloride is slowly treated with oxalyl chloride (88 mL, 1.00 mole), with cooling, stirred at ambient temperatures for 16 hours, treated with ethyl vinyl ether (72.1 g, 1.00 mole) over a 1 hour period and stirred at ambient temperatures for 16 hours. This reaction mixture is treated sequentially with diethyl oxalacetate (199.28 g, 1.06 mole) and (with cooling) triethylamine (224 g, 2.2 mole), stirred for 0.5 hours and treated with a premixed solution of concentrated HCl (200 ml) and concentrated $NH_4OH$ (200 ml) in 100 ml of water. The reaction mixture is treated further with water (250 ml), concentrated $NH_4OH$ (70 ml) and acetic acid (200 ml). The resultant mixture is distilled under $N_2$ at 88° C. and atmosphere pressure to remove 1850 g of distillate. The distillation pot is then treated with absolute ethanol (1.0 L) and $NH_4OCOCH_3$ (180 g), heated at reflux temperature for 16 hours and distilled at 100° C. to remove 887 g of distillate. The distillation pot is cooled and the residue is partitioned between water and 2:1 ethyl acetate/hexanes. The organic phase is separated, washed sequentially with water and brine and concentrated in vacuo to give the title product as an oil, 179.5 g, (77% pure) 58.5% yield, identified by NMR analysis.

EXAMPLES 2–7

Using essentially the same procedure described in Example 1, and employing the appropriately substituted vinyl ether substrate, the results shown in Table I are obtained.

TABLE I

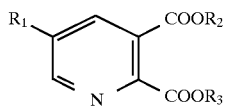

$$\text{2)} \xrightarrow{\text{DOX}^1}{\text{base}} \quad \text{3)} \xrightarrow{\text{NH}_4^\oplus Y^\ominus}{\text{(2nd solvent)}}$$

[Product structure: pyridine with $R_1$ at 5-position, $CO_2C_2H_5$ groups at 2 and 3 positions]

| Example Number | R | $R_1$ | acid chloride (1st solvent) | base (Molar-equivalents) | $Y^\ominus$ (2nd solvent) | % yield |
|---|---|---|---|---|---|---|
| 2 | nBu | H | oxalyl chloride (ClCH$_2$CH$_2$Cl) | Triethylamine (2.2) | $^\ominus$OCOCH$_3$ (C$_2$H$_5$OH) | 52.8 |
| 3 | nBu | H | oxalyl chloride (ClCH$_2$CH$_2$Cl) | Pyridine (2.2) | $^\ominus$OCOCH$_3$ (C$_2$H$_5$OH) | 39.6 |
| 4 | C$_2$H$_5$ | H | POCl$_3$ (CH$_2$Cl$_2$) | Triethylamine (3.5) | $^\ominus$OCOCH$_3$ (C$_2$H$_5$OH) | 62.3 |
| 5 | C$_2$H$_5$ | CH$_3$ | oxalyl chloride (CH$_2$Cl$_2$) | Triethylamine (2.5) | $^\ominus$SO$_3$NH$_2$ (CH$_3$CO$_2$H) | 48 |
| 6 | C$_2$H$_5$ | C$_2$H$_5$ | oxalyl chloride (CH$_2$Cl$_2$) | Triethylamine (2.5) | $^\ominus$OCOCH$_3$ (CH$_3$CO$_2$H) | 42 |
| 7 | CH$_3$ | CH$_2$OCH$_3$ | POCl$_3$ (CH$_2$Cl$_2$) | Triethylamine (3.5) | $^\ominus$OH (H$_2$O/CH$_3$CO$_2$C$_2$H$_5$) | 17.7 |

Diethyl oxalacetate

I claim:

1. A process for the preparation of a compound of formula I

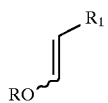

wherein
$R_1$ is H or $C_1$–$C_4$alkyl optionally substituted with $C_1$–$C_4$alkoxy or halogen; and
$R_2$ and $R_3$ are each independently $C_1$–$C_6$alkyl which comprises a) reacting an alkyl vinyl ether compound of formula II

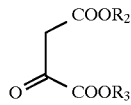

wherein the formula II compound is the cis isomer, the trans isomer or a mixture thereof, R is $C_1$–$C_4$alkyl and $R_1$ is as defined for formula I with at least one molar equivalent of Vilsmeier reagent optionally in the presence of a first solvent to form a first intermediate;

b) reacting said first intermediate with at least one molar equivalent of an oxalacetate of formula III

[Structure III: O=C with COOR$_2$ and COOR$_3$ groups]

wherein
$R_2$ and $R_3$ are as defined for formula I in the presence of at least two molar equivalents of an organic amine base to form a second intermediate; and c) reacting said second intermediate with an ammonia source optionally in the presence of a second solvent to form the formula I pyridine diester product.

2. The process according to claim 1 wherein a first solvent is present.

3. The process according to claim 2 wherein the first solvent is a halogenated hydrocarbon.

4. The process according to claim 3 wherein the first solvent is dichloroethane or methylene chloride.

5. The process according to claim 1 wherein the base is triethylamine.

6. The process according to claim 1 wherein a second solvent is present.

7. The process according to claim 6 wherein the second solvent is a $C_1$–$C_4$alkanol or a $C_1$–$C_4$carboxylic acid or a mixture thereof.

8. The process according to claim 7 wherein the second solvent is ethanol or acetic acid or a mixture thereof.

9. The process according to claim 8 wherein the ammonia source is ammonium acetate.

10. The process according to claim 5 wherein a second solvent is present and the ammonia source is ammonium acetate.

11. The process according to claim 1 wherein $R_1$ is H, methyl, ethyl or methoxymethyl.

12. The process according to claim 5 wherein $R_1$ is H, methyl, ethyl or methoxymethyl.

13. The process according to claim 10 wherein $R_1$ is H.

14. The process according to claim 10 wherein $R_1$ is ethyl or methyl.

15. The process according to claim 12 wherein $R_3$ and $R_4$ are each independently methyl or ethyl.

* * * * *